United States Patent

Yemoto et al.

[11] Patent Number: 4,500,725
[45] Date of Patent: Feb. 19, 1985

[54] SILANE DERIVATIVE AND FRAGRANT ARTICLE

[75] Inventors: Jiichiro Yemoto, Kumamoto; Ryokichi Tarao, Kanagawa; Yoshio Yamamoto, Kumamoto, all of Japan

[73] Assignee: Chisso Corporation, Osaka, Japan

[21] Appl. No.: 402,811

[22] Filed: Jul. 28, 1982

[30] Foreign Application Priority Data

Jul. 30, 1981 [JP] Japan ............................. 56-119641
Nov. 24, 1981 [JP] Japan ............................. 56-187950

[51] Int. Cl.$^3$ ............................. C07F 7/04; C07F 7/08; C07F 7/18
[52] U.S. Cl. ................................ 556/482; 556/483; 252/522 R
[58] Field of Search ............................. 556/482, 483

[56] References Cited

U.S. PATENT DOCUMENTS 2,723,210 11/1955 Biefeld .......................... 556/482 X
3,215,719 11/1965 Allen et al. ..................... 556/482
4,294,975 10/1981 Takago et al. ................... 556/482

FOREIGN PATENT DOCUMENTS 1439013 12/1966 France ........................... 556/482
1436568 1/1967 France ........................... 556/482

*Primary Examiner*—Paul F. Shaver

*Attorney, Agent, or Firm*—Wenderoth, Lind & Ponack

[57] ABSTRACT

A compound represented by the general formula:

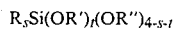

wherein R represents methyl, ethyl, or vinyl; R'O represents

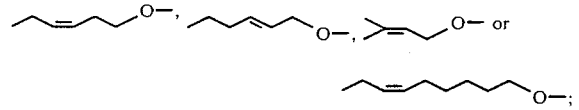

R" represents methyl or ethyl; s represents 0 or 1; and t represents an integer of from 1 to 4; and fragrant agent formed by impregnating solid matter with a compound represented by the general formula:

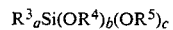

wherein $R^3$, $R^4$ and $R^5$ represent a hydrocarbon group, with the proviso that $R^5$ is derived from an alcohol of the general formula $R^5OH$ that develops aroma; and a, b and c are each an integer, or a derivative thereof.

7 Claims, No Drawings

SILANE DERIVATIVE AND FRAGRANT ARTICLE

BACKGROUND OF THE INVENTION

1. Field of the Invention

This invention relates to a novel organic silicate ester compound with persistent aroma and an impregnation-type fragrant article using the organic silicate ester compound.

2. Description of the Prior Art

It is generally known that a liquid or solid fragrant article is used for persistent aroma. Among such fragrant articles, the type of articles that are produced by impregnating fibrous materials or porous moldings with fragrant components, and that gradually volatilize their fragrant components when in use, have such features as the capability of impregnating fragrant components by a simple process and ease and simplicity of handling in use. Such articles are however insufficient to display the effect of emitting, for a long period of time, aroma strong enough to be sensed during volatilization of the perfume-imparting component.

The use of an organic silicate este compound having persistent aroma can be found, for example, in the following literatures.

U.S. Pat. No. 3,215,719 by Allen et al. discloses that a silicate ester represented by the general formula:

$$(RO)_a Si(OR')_b (R'')_{(4-a-b)}$$

wherein RO represents an organic hydroxy group selected from the group consisting of an eugenoxy, $\beta$-phenylethoxy and cinnamyloxy; R' represents a monovalent group selected from alkyl and phenyl; and R'' represents methyl, is used for treatment of fabric materials. The patent indicates that when an emulsifying agent and an aqueous dispersion medium are applied to the fabric materials, the smell remains even after it is washed, for example, 20 times; and that if it is desired to deposit a large amount of the silicate ester on the surface of the fabric materials, it can be applied without dilution when the silicate ester is in a liquid state and the fabric materials are dried after impregnation.

Regarding the use of aroma-providing components based on a silicon compound, there are known compositions comprising at least one type of silicon compound which have at least one of the groups of the general formula —OR (where R denotes a residue which remains after the removal of a hydroxy group from cyclic or acyclic monoterpene alcohol, essential aryl-substituted aliphatic alcohol, and essential aliphatic-substituted phenol) and other substituents selected from hydrogen and organic groups free of sulfur and phosphorus, said groups and substituents being bonded to the silicon by a silicon-carbon (hydrogen) bond or a silicon-oxygen-carbon (hydrogen) bond.

As examples of compositions comprising one or more of such silicon compounds, there may be mentioned a knitted fabric conditioner composition containing an aliphatic alkyl quatenary ammonium compound (Japanese Patent Application Lain-open No. 59498/79); a composition containing powdery or granular detergent (Japanese Patent Application Laind-open No. 93006/79); a sweat-controlling or deodorant composition containing an astringent substance or antibacterial substance (Japanese Patent Application Laid-open No. 127314/80); and a soap composition (Japanese Patent Application Laid-open No. 129499/80), all these compositions being described as imparting persistent aroma during use.

None of the above literatures, however, discloses a silicate ester derived from aroma-providing alcohol having 9 or less carbon atoms, not do they disclose the use of a general organic silicate ester compound as a fragrant article.

SUMMARY OF THE INVENTION

The object of this invention is to provide a novel fragrant organic ester compound and an impregnation-type fragrant article with improved durability, using such organic ester compound.

This invention relates to a silane derivative and a fragrant article as shown in the following:

1. Silane derivative represented by the general formula:

$$R_s Si(-OR')_t(-OR'')_{4-s-t} \qquad (I)$$

wherein R represents $CH_3-$, $CH_3CH_2-$ or $CH_2=CH-$; R'O represents

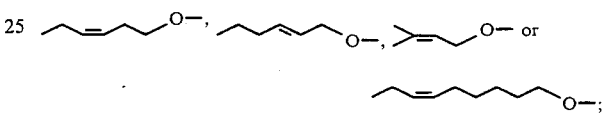

R''O represents $CH_3O-$ or $CH_3CH_2O-$; s represents 0 or 1; and t represents an integer of from 1 to 4, respectively.

2. Fragrant article formed by impregnating a solid material having a plurality of open-ended voids on the surface, with one or more of aromatizing components selected from the compounds represented by the general formulae:

$$R^3{}_a Si(OR^4)_b(OR^5)_c \qquad (II)$$

and $$[R^3{}_j Si(OR^4)_k(OR^5)_e(OH)_m O_n]_p \qquad (III)$$

wherein $R^3$ is selected from the group consisting of hydrogen, a saturated or unsaturated aliphatic hydrocarbon group, an aromatic hydrocarbon group, an aliphatic hydrocarbon substituted aromatic hydrocarbon group, and an aromatic hydrocarbon substituted aliphatic hydrocarbon group, the hydrocarbon groups having 1 to 10 carbon atoms; $R^4$ is an alkyl or an alkenyl group having 1 to 5 carbon atoms; $R^5$ is selected from the group consisting of a saturated or unsaturated aliphatic hydrocarbon group, an aromatic hydrocarbon group, an aliphatic hydrocarbon substituted aromatic hydrocarbon group and an aromatic hydrocarbon substituted aliphatic hydrocarbon group, the hydrocarbon groups having 4–15 carbon atoms, with the proviso that the $R^5$ develops aroma in the form of $R^5 OH$; each of $R^3$, $R^4$ and $R^5$ may be the same or different if two or more thereof are present in the same molecule; a is an integer of from 0 to 3, b is an integer of from 0 to 3, c is an integer of from 1 to 4, provided that $a+b+c=4$, j and m are each a numeral from zero to 3 inclusive, $0 \leq k \leq 4$, $0 < e < 4$, $0 \leq n < 2$, $j+k+e+m+2n=4$, and p is a positive integer.

The compound represented by the formula (I) of this invention is useful as a long-life material for perfume that imparts durable of aroma to highly volatile cis-3- hexenol (IV), trans-2-hexenol (V), pulenol (VI) and cis-6-nonenol (VII).

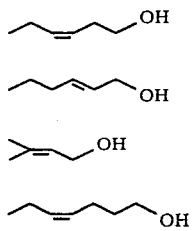

The compound (I) of this invention can be obtained by reacting tetrachloro silane, methyl trichloro silane, ethyl trichloro silane or vinyl trichloro silane with the compound (IV), (V), (VI) or (VII), followed by reacting the remaining chlorine with sodium ethylate and/or sodium methylate. The compound (I) is preferably obtained by an alcohol exchange reaction between tetraethoxy silane, tetramethoxy silane, methyl triethoxy silane, methyl trimethoxy silane, ethyl triethoxy silane, ethyl trimethoxy silane, vinyl triethoxy silane, or vinyl trimethoxy silane and the compound (IV), (V), (VI) or (VII).

In the above-mentioned general formulae (II) and (III), $R^3$ is a saturated or unsaturated hydrocarbon group such as methyl, ehtyl, propyl, vinyl, allyl, or phenyl, and the like, for example. Of these groups, it is preferable to use the groups having 1 to 4 carbon atoms, because of the rapid formation reaction of the compound (II) or (III) and the ready availability of their sources.

In the general formulae (II) and (III), $R^4$ and $R^5$ are residues which remain after a hydroxyl group is removed from the corresponding alcohols. $R^5$ is what is gradually liberated as $R^5OH$ from the compound (II) or (III) by subjecting the same to hydrolysis, and is volatilized into the atmosphere to create the aroma. $R^4$ is what remains, for example, in the compound (II) after alcohol substitution is performed by reacting an organic silicon compound, the starting material for the compound (II), represented by the general formula:

$$R^3{}_xSi(OR^4)_{4-x}$$

(where x is 0, 1, 2, or 3) with an aroma developing alcohol compound of the general formula: $R^5OH$.

Illustrative of alcohol $R^4OH$ corresponding to $R^4$ are methanol, ethanol, n-propanol, iso-propanol, n-butanol, iso-butanol, sec-butanol, and pentanol including n-pentanol, methyl butanol, etc. It is preferable to use $R^4$ having 1 to 3 carbon atoms, because of the rapid formation reaction of the compound (II) or (III) and the ready availability of their sources.

Examples of alcohol $R^5OH$ corresponding to $R^5$ include a saturated aliphatic alcohol, such as n-butanol, iso-butanol, sec-butanol, pentanol including n-pentanol, methyl butanol, etc., hexanol including n-hexanol, methyl pentanol, ethyl butanol, etc., and the like; an unsaturated alcohol, such as pulenol, cis-3-hexenol, trans-2-hexenol, sorbyl alcohol, cis-4-heptenol, trans-2-octenol, trans-4-decenol, trans-2-cis-6-nonadienol, geraniol, citronellol, nerol, etc., an aliphatic hydrocarbon substituted phenol, such as eugenol, vanillin, 4-(p-hydroxyphenyl)-2-butanon etc., and an aromatic hydrocarbon substituted aliphatic alcohol, such as β-phenylethyl alcohol, cinnamic alcohol, benzyl alcohol, etc.

Alcohols having 4 or 5 carbon atoms, such as n-butanol and pentanol are given as examples of both $R^4OH$ and $R^5OH$, but they can be of either type. Namely, they may be introduced into the compound (II) or (III) as a fragrant component $R^5O$; or into the compound (II) or (III) as $R^4O$ directly from a raw material compound of the general formula:

$$R_xSi(OR')_{4-x}$$

though it is not a desired fragrant component.

Of the above-mentioned alcohols given as $R^5OH$, the alcohols having 8 or less of carbon atoms, such as trans-2-octenol, cis-3-hexenol, trans-2-hexenol, and pulenol are fragrant compounds which are the so-called "top note", and give a refreshing feeling. They are however highly volatile, and therefore tend to be lost in a short period of time. This problem has been solved by using them in the form of the compound (II) or (III).

As examples of the molecular formulae for the compounds represented by the general formula (II), there are mentioned the following:

| | |
|---|---|
| $CH_2=CHSi(OC_2H_5)_b(OC_6H_{11})_c$ | for cis-3-hexenol (molecular formula $C_6H_{11}OH$); |
| $CH_3Si(OCH_3)_b(OC_{10}H_{17})_c$ | for geraniol (molecular formula $C_{10}H_{17}OH$); |
| $CH_3Si(OC_2H_5)_b(OC_6H_{11})_c$ | for trans-3-hexenol (molecular formula $C_6H_{11}OH$); |
| $CH_3Si(OC_2H_5)_b(OC_8H_9)_c$ and the like. | for 2-phenylethyl alcohol (molecular formula $C_8H_9OH$); |

The compound represented by the general formula (II) is produced, for example, by reacting the organic silicon compound represented by the general formula:

$$R^3{}_xSi(OR^4)_{4-x}$$

with an alcoholic compound represented by $R^5OH$, thereby utilizing the reaction of substituting a part or all of the $-OR^4$ group of the organic silicon compound with an $-OR^5$ group. The reaction can be carried out at an ambient temperature but, preferably is performed at an elevated temperature. Catalysts usable for this reaction include titanium alkoxide, stannous octylate, potassium carbonate, methyl trichloro silane, sodium paratoluensulfonate, etc. When it is desired that the catalyst does not remain in the reaction product, the reaction can be performed without using a catalyst. It is preferable in the reaction to add a step which comprises removing $R^4OH$ formed by substitution reaction, from the reaction system by means of reflux, for example.

The compound represented by the general formula (II) is considered to be formed accompanied by a plurality of compounds, as shown by the examples to be mentioned later.

Another method for producing the compound represented by the general formula (II) is, for example, to utilize the reaction of the above-mentioned alcoholic compounds $R^4OH$ and $R^5OH$ with a silicon compound having a siliconhalogen bond and/or silicon-acyloxy bond, such as methyl trichloro silane, vinyl acetoxy silane, etc. The reaction can be performed at ambinet temperature or elevated temperature, for example, without using a catalyst under atmospheric or normal pressure, or by using a catalyst, such as an amine compound, pyridine compound, etc. When importance is attached to the absence of the residual catalyst in the reaction product, it is preferable to perform the reaction without using a catalyst. (The synthetic method is also described in Indian J. Chem. Vol. 12, Oct. 1974, pp. 1099–1101 and Vol. 13, Dec. 1975, pp. 1364–1365.)

The compound represented by the general formula (III) may be a compound which can be produced by a partial hydrolysis of the compound represented by the above-mentioned general formula (II), or a compound which can be produced by dehydration condensation of the compound produced by partial hydrolysis. The former can be produced by adding water to the compound of the general formula (II), preferably followed by heating, and finally removing $R^4OH$ and/or $R^5OH$ formed by the hydrolysis, from the reaction system by distillation, if necessary. The latter can be obtained by the condensation of the former, using an acid or an alkali as a catalyst, or without using a catalyst, as shown in Organo-silicon Compounds 1 (published by Academic Press, 1965, p. 41).

The afore-mentioned solid matter having a plurality of open-ended voids on its surface, which is used in combination with fragrant components, forms the so-called "base material" for the impregnation-type fragrant agent. Examples of such solid matters are woven fabric, non-woven fabric, knitted goods and felt-like material made of metal, asbestos, rock wool, cellulose, wool or synthetic fiber; Japanese paper, tissue paper, corrugated cardboard; continuously or discontinuously foamed material; a bundle of fine glass tubes, aluminum foil bent zigzag and piled on or joined to another aluminum foil or the like; and aggregated beads, sinter, unglazed chinaware, vermiculite, and zeolite.

These solid matters hving openings on their surfaces can be impregnated or used by covering them partially with a film or foil having small permeability for gas and/or moisture.

The following methods can be used for impregnating the above-mentioned solid matters having openings on their surfaces with the above-mentioned aroma-imparting components. This can be done by dipping the solid matter in a liquid or solution of the aroma-imparting component; or by dropping, pouring, spraying or otherwise applying a liquid or solution of the aroma-imparting component to the solid matter to bring them in contact. The aroma-imparting components can be mixed with substances which have no or a favorable influence on the aroma of the components, such as propylene glycol, alcohols, aldehydes, ketones, etc. before impregnation into the solid matter.

Although this invention has been described with respect to a number of details, it is not intended that this invention should be limited thereby. Moreover, the examples which follow are intended solely to illustrate a variety, including the most favorable, embodiments of this invention and are not intended in any way to limit the scope and intent of this invention.

EXAMPLE 1

With a packed tower and a reflux condenser attached to a 300 ml flask, 89.2 g (equivalent to 0.5 mol) of methyltriethoxysilane ($CH_3Si(OC_2H_5)_3$) and 150.2 g (equivalent to 1.5 mol.) of trans-2-hexenol

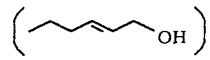

were put in the flask and then heated up to 150° to 200° C. in an atmosphere of nitrogen under normal pressure. The distillation of ethanol ended after b 12 hours, when heating was stopped. After the residual ethanol was distilled and removed under a reduced pressure (90° to 155° C., 100 to 150 mmHg, 1 hr.), the reaction product was analyzed by gas chromatography and the following results were obtained.

| Compound No. | Estimated structure | Concentration (GC %) |
|---|---|---|
|  | ~~~OH | 11.7 |
| (XIII) | $CH_3Si(O$~~~$)(OC_2H_5)_2$ | 2.0 |
| (XII) | $CH_3Si(O$~~~$)_2(OC_2H_5)$ | 19.1 |
| (XI) | $CH_3Si(O$~~~$)_3$ | 65.5 |

(XI) $CH_3Si(O$~~~$)_3$

Colorless liquid (isolated by distillation, 99.3 GC %)
bp. 174° C./6 mm Hg

IR(NaCl) $1670^{-1}$, $970\ cm^{-1}$ ( $\overset{H}{\underset{H}{>}}C=C<$ )

$1100\ cm^{-1}$, $1060\ cm^{-1}$ (Si—O—C)
MS measured value $M^+$: 340
calculated value M: 340

NMR(CDCl$_3$) δ 0.14(3H, s, $\geq$Si—CH$_3$);

0.89 (9H, t, J = 6.8 Hz, —CH$_2$—CH$_3$);
1.13–1.70 (6H, m, —CH$_2$—CH$_2$—CH$_3$);
1.76–2.24 (6H, m, —CH=CH—CH$_2$—CH$_2$—);
4.22 (6H, d, J = 4.1 Hz, —O—CH$_2$—CH=CH—);
5.62 (6H, m, —CH$_2$—CH=CH—CH$_2$—) ppm (XII) $CH_3Si(O$~~~$)_2(OCH_2CH_3)$ GC—MS Measured value $M^+$: 286
Calculated value M: 286

(XIII) $CH_3Si(O$~~~$)(OCH_2CH_3)_2$

GS—MS Measured value $M^+$: 232
Calculated value M: 232

EXAMPLE 2

In a manner similar to that of Example 1, 85.8 g (equivalent to 0.4 mol) of tetraethoxysilane (Si-(OCH$_2$CH$_3$)$_4$) and 161.5 g of trans-2-hexenol

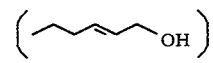

(equivalent to 1.6 mol) were heated in an atmosphere of nitrogen up to 150° C. to 200° C. under normal pressure. The heating was stopped after 13.5 hours when the distillation of ethanol ended. After ethanol present in the reaction product was distilled and removed, the reaction product was analyzed by gas chromatography, and the following results were obtained.

| No. of compound | Estimated structure | Concentration (GC %) |
|---|---|---|
| | ~~~~OH | 9.2 |
| (XVI) | (~~~~O)₂Si(OC₂H₅)₂ | 3.2 |
| (XV) | (~~~~O)₃Si(OC₂H₅) | 21.2 |
| (XIV) | (~~~~O)₄Si | 64.2 |

(XIV) (~~~~O)₄Si

Colorless liquid (isolated by distillation; 97.0 GC %)
bp. 210–212° C./5 mm Hg

IR(NaCl) 1670, 970 cm⁻¹ ( $\overset{H}{\underset{}{>}}C=C\overset{}{\underset{H}{<}}$ )

1100, 1060 cm⁻¹ (Si—O—C)
MS Measured value M⁺, 424
Calculated value M, 424
NMR (CDCl₃) δ 0.89 (12H, t, J = 6.8 Hz, —CH₂—CH₃);
1.12–1.69 (8H, m, —CH₂—CH₂—CH₃);
1.72–2.22 (8H, m, —CH=CH—CH₂—CH₂—);
4.24 (8H, d, J = 4.1 Hz, —O—CH₂—CH=CH—);
5.61 (8H, m, —CH₂—CH=CH—CH₂—) ppm (XV) (~~~~O)₃Si(OCH₂CH₃)

GC—MS Measured value M⁺: 370
Calculated value M: 370

(XVI) (~~~~O)₂Si(OCH₂CH₃)₂

GC—MS Measured value M⁺: 316
Calculated value M: 316

| Compound No. | Estimated structure | Concentration (GC %) |
|---|---|---|
| | ~~~~OH | 7.2 |
| (XIX) | CH₃Si(O~~~~)(OC₂H₅)₂ | 1.1 |
| (XVIII) | CH₃Si(O~~~~)₂(OC₂H₅) | 16.2 |
| (XVII) | CH₃Si(O~~~~)₃ | 74.7 |

(XVII) CH₃Si(O~~~~)₃

Colorless liquid (isolated by distillation; 99.4 GC %)
bp. 169° C./5 mm Hg

IR(NaCl) 1655, 720 cm⁻¹ ( $\overset{H}{\underset{}{>}}C=C\overset{H}{\underset{}{<}}$ )

1090 cm⁻¹ (Si—O—C)
MS Measured value M⁺: 340
Calculated value M: 340

NMR(CDCl₃) δ 0.12 (3H, s, ≧Si—CH₃);

0.96 (9H, t, J = 7.4 Hz, —CH₂—CH₃);
1.68–2.49 (12H, m, R—CH₂—CH=CH—;
R— is CH₃— or —CH₂—);
3.72 (6H, t, J = 7.1 Hz, —O—CH₂—CH₂—);
5.40 (6H, m, —CH₂—CH=CH—CH₂—) ppm (XVIII) CH₃Si(O~~~~)₂(OC₂H₅)

GC—MS Measured value M⁺: 286
Calculated value M: 286

(XIX) CH₃Si(O~~~~)(OC₂H₅)₂

GC—MS Measured value M⁺: 232
Calculated value M: 232

EXAMPLE 3

In a manner similar to that of Example 1, 89.2 g (equivalent to 0.5 mol) of methyltriethoxysilane (CH₃Si(OC₂H₅)₃) and 150.2 g (equivalent to 1.5 mol) of cis-3-hexenol

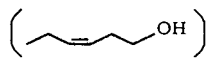

were heated up to 170° C. in the beginning and 200° C. at the end in an atmosphere of nitrogen under normal pressure. The distillation of ethanol ended after 12 hours, when heating was stopped. After ethanol present in the reaction product was distilled and removed under reduced pressure, the reaction product was analyzed by gas chromatography, and the following results were obtained.

EXAMPLE 4

In a manner similar to that of Example 1, 78.3 g (equivalent to 0.4 mol) of vinyltriethoxysilane (CH₂=CH—Si (OC₂H₅)₃) and 124.1 g (equivalent to 1.2 mol) of cis-3-hexenol

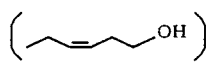

were heated up to 160° C. to 200° C. in an atmosphere of nitrogen under normal pressure. The distillation of ethanol ended after 24 hours, when heating was stopped. After residual ethanol was distilled and removed under reduced pressure, the reaction product was analyzed by gas chromatography, and the following results were obtained.

| Compound No. | Estimated structure | Concentration (GC %) |
|---|---|---|
| | ~~~OH (with double bond) | 12.6 |
| (XXII) | CH$_2$=CHSi(O~~~~)(OC$_2$H$_5$)$_2$ | 1.8 |
| (XXI) | CH$_2$=CHSi(O~~~~)$_2$(OC$_2$H$_5$) | 18.0 |
| (XX) | CH$_2$=CHSi(O~~~~)$_3$ | 64.8 |
| (XX) | CH$_2$=CHSi(O~~~~)$_3$ | |

Colorless liquid (isolated by distillation; 95.6 GC %)
bp. 175° C./5 mmHg
IR(NaCl) 1600 cm$^{-1}$ (CH$_2$=CH—),
1090 cm$^{-1}$ (Si—O—C)

1655, 720 cm$^{-1}$ ( $\ce{>C=C<}$ with H's )

MS Measured value M$^+$:352
Calculated value M:352
NMR(CDCl$_3$) δ 0.96(9H, t, J=7.4 Hz, —CH$_2$—CH$_3$);
1.67–2.50(12H, m, R—CH$_2$—CH=CH—;
R— is CH$_3$— or —CH$_2$—);
3.74(6H, t, J=7.2 Hz, —O—CH$_2$—CH$_2$—);
5.40(6H, m, —CH$_2$—CH=CH—CH$_2$—);

6.00(3H, m, $\ce{>Si-CH=CH2}$)ppm (XXI) CH$_2$=CHSi(OC$_2$H$_5$)(O~~~~)$_2$

GC—MS Measured value M$^+$:298
Calculated value M:298

(XXII) CH$_2$=CHSi(OC$_2$H$_5$)$_2$(O~~~~)

GC—MS Measured value M$^+$:244
Calculated value M:244

| Compound No. | Estimated structure | Concentration (GC %) |
|---|---|---|
| | ~~~OH | 13.6 |
| (XXV) | CH$_3$Si(O~~~~)(OC$_2$H$_5$)$_2$ | 2.3 |
| (XXIV) | CH$_3$Si(O~~~~)$_2$(OC$_2$H$_5$) | 21.1 |
| (XXIII) | CH$_3$Si(O~~~~)$_3$ | 61.9 |
| (XXIII) | CH$_3$Si(O~~~~)$_3$ | |

Colorless liquid (isolated by distillation; 99.4 GC %)
bp. 255° C. (9 mmHg)

IR(NaCl) 1655, 720 cm$^{-1}$ ( $\ce{>C=C<}$ with H's )

1097 cm$^{-1}$ (Si—O—C)
MS Measured value M$^+$:466
Calculated value M:466

NMR(CDCl$_3$) δ 0.11(3H, s, $\ce{>Si-CH3}$);

0.95(9H, t, J=7.4 Hz, —CH$_2$—CH$_3$);
1.12–1.72(18H, m, —CH$_2$—CH$_2$—CH$_2$—);
1.72–2.30(12H, m, R—CH$_2$—CH=CH—;
R— is CH$_3$— or —CH$_2$—);
3.71(6H, t, J=6.3 Hz, —OCH$_2$CH$_2$—);
5.33(6H, m, —CH$_2$—CH=CH—CH$_2$—)
ppm (XXIV) CH$_3$Si(OC$_2$H$_5$)(O~~~~)$_2$ GC—MS Measured value M$^+$:370
Calculated value M:370

(XXV) CH$_3$Si(OC$_2$H$_5$)$_2$(O~~~~)

GC—MS Measured value M$^+$:274
Calculated value M:274

EXAMPLE 5

Here, 16.7 g (equivalent to 0.09 mol) of methyltriethoxysilane (CH$_3$Si(OC$_2$H$_5$)$_3$) and 40.0 g (equivalent to 0.27 mol) of cis-6-nonenol

were put in a 100 ml flask provided with a packed column and reflux condenser and were heated up to 190° to 235° C. in an atmosphere of nitrogen under normal pressure. Heating was stopped when the distillation of ethanol ended (6 hours after ethanol started distillation). Then residual ethanol was distilled and removed under reduced pressure.

The analytical results of the product produced in the reactor as determined by gas chromatography were as follows.

EXAMPLE 6

In a manner similar to that of Example 5, 45.6 g (equivalent to 0.18 mol) of methyltriethoxysilane (CH$_3$Si(OC$_2$H$_5$)$_3$) and 31.2 g (equivalent to 0.53 mol) of pulenol

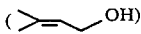

were heated up to 140° C. to 190° C. in an atmosphere of nitrogen under normal pressure. The distillation of ethanol ended after 16.5 hours, when heating was stopped. Then after residual ethanol was distilled and removed under reduced pressure, the reaction product was analyzed by gas chromatography and the following results were obtained.

| Compound No. | Estimated structure | Concentration (GC %) |
|---|---|---|
| | >=\_OH | 16.9 |
| (XXVIII) | CH₃Si(O \~=<)(OC₂H₅)₂ | 7.8 |
| (XXVII) | CH₃Si(O \~=<)₂(OC₂H₅) | 20.1 |
| (XXVI) | CH₃Si(O \~=<)₃ | 45.2 |

(XXVI) CH₃Si(O \~=<)₃

Colorless liquid (isolated by distillation; 97.4 GC %)
bp. 152–143° C./5 mmHg

IR(NaCl) 1680 cm⁻¹ (—CH—C$\stackrel{\angle}{\diagdown}$)

1070 cm⁻¹ (Si—O—C)
MS Measured value M⁺:298
Calculated value M:298

NMR(CDCl₃) δ 0.14(3H, s, CH₃—Si$\stackrel{\angle}{\diagdown}$);

1.70(18H, m, (CH₃)₂C=CH—);
4.28(6H, d, J=6.9 Hz,

—O—CH₂—CH=C$\stackrel{\angle}{\diagdown}$);

5.36(3H, m, —O—CH₂—CH=C$\stackrel{\angle}{\diagdown}$) ppm (XXVII) CH₃Si(O \~=<)₂(OCH₂CH₃)

GC—MS Measured value M⁺:258
Calculated value M:258

(XXVIII) CH₃Si(O \~=<)(OCH₂CH₃)₂

GC—MS Measured M⁺:218
Calculated value M:218

EXAMPLE 7

In a manner similar to that of Example 5, 29.3 g (equivalent to 0.21 mol) of methyltrimethoxysilane (CH₃Si(OCH₃)₃) and 43.5 g (equivalent to 0.43 mol) of cis-3-hexenol

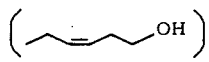

were heated up to 120° C. to 220° C. in an atmosphere of nitrogen under normal pressure. The distillation of methanol ended after 10 hours, when heating was stopped. After residual methanol was distilled and removed under reduced pressure, the reaction product was analyzed by gas chromatography, and the following results were obtained.

| Compound No. | Estimated structure | Concentration (GC %) |
|---|---|---|
| | \~=\_OH | 1.2 |
| (XXXI) | CH₃Si(O\~=\~)(OCH₃)₂ | 13.0 |
| (XXX) | CH₃Si(O\~=\~)₂(OCH₃) | 42.7 |
| (XXIX) | CH₃Si(O\~=\~)₃ | 41.1 |

(XXIX) CH₃Si(O\~\~=\~)₃

GC—MS Measured value M⁺: 258
Calculated value M: 258

(XXX) CH₃Si(O\~\~=\~)₂(OCH₃)

GC—MS Measured value M⁺: 272
Calculated value M: 272

(XXIX) CH₃Si(O\~\~=\~)(OCH₃)₂

GC—MS Measured value M⁺: 204
Calculated value M: 204

EXAMPLE 8

Here, 53.0 g (equivalent to 0.27 mol) of ethyltriethoxysilane (CH₃CH₂Si(OC₂H₅)₃) and 67.5 g (equivalent to 0.64 mol) of trans-2-hexenol

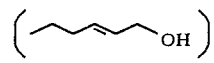

were put in a 300 ml flask provided with a packed column and reflux condenser and were heated in an atmosphere of nitrogen under normal pressure. Heating was stopped when the temperature in the reactor reached 150° C. The pressure was lowered down to 200 mmHg, followed by another heating up to 150° C. This procedure was repeated in order of 150 mmHg, 100 mmHg and 50 mmHg (heated up to 150° C. respectively).

The reaction product thus obtained was analyzed by gas chromatography and the following results were obtained.

| Compound No. | Estimated structure | Concentration (GC %) |
|---|---|---|
| | \~\~\_OH | 0.8 → 1.1 |
| (XXXIV) | C₂H₅Si(O\~=\~)(OC₂H₅)₂ | 12.0 → 16.4 |
| (XXXIII) | C₂H₅Si(O\~=\~)₂(OC₂H₅) | 27.8 → 38.1 |
| (XXXII) | C₂H₅Si(O\~=\~)₃ | 28.5 → 39.0 |

-continued

| Compound No. | Estimated structure | Concentration (GC %) |
|---|---|---|
| (XXXII) | $CH_3CH_2Si(O\diagup\diagdown\diagup)_3$ | |

Colorless liquid
bp. 198–200° C./9 mm Hg

IR(NaCl) 1670, 973 cm$^{-1}$ ( $\underset{H}{\overset{H}{>}}C=C<$ )

1108, 1065 cm$^{-1}$ (Si—O—C)
MS Measured value M$^+$: 354
Calculated value M: 354
NMR(CDCl$_3$) δ

0.30–1.04 (14H, m, $>$Si—CH$_2$CH$_3$, —CH$_2$CH$_2$CH$_3$);

1.10–1.76 (6H, m, —CH$_2$—CH$_2$—CH$_3$);
1.76–2.24 (6H, m, —CH=CH—CH$_2$—CH$_2$—);
4.22 (6H, d, J = 4.1 Hz, —O—CH$_2$—CH=CH—);
5.61 (6H, m, —CH$_2$—CH=CH—CH$_2$—) ppm (XXXIII) $CH_3CH_2Si(O\diagup\diagdown\diagup)_2(OC_2H_5)$ GC—MS Measured value M$^+$: 300
Calculated value M: 300

(XXXIV) $CH_3CH_2Si(O\diagup\diagdown\diagup)(OC_2H_5)_2$

GC—MS Measured value M$^+$: 246
Calculated value M: 246

EXAMPLE 9

A 300 ml flask was provided with a packed column and reflux condenser, and 38.2 g (equivalent to 0.2 mol) of vinyltriethoxysilane (CH$_2$=CHSi(OC$_2$H$_5$)$_3$) and 65.2 g (equivalent to 0.6 mol) of cis-3-hexenol (C$_6$H$_{11}$OH) were put in the flask to be heated up to 145° C. to 170° C. in an atmosphere of nitrogen under normal pressure. Heating was stopped after 17 hours when the distillation of ethanol ended. After ethanol present in the reaction product was distilled and removed (100° C. to 135° C., absolute pressure 60 mmHg to 200 mmHg, 2.5 hours), the reaction product was analyzed by gas chromatography and the following results were obtained.

| | | |
|---|---|---|
| | C$_6$H$_{11}$OH | 2.4 weight % |
| | CH$_2$=CHSi(OC$_2$H$_5$)$_2$(OC$_6$H$_{11}$) | 10.4 weight % |
| | CH$_2$=CHSi(OC$_2$H$_5$)(OC$_6$H$_{11}$)$_2$ | 37.3 weight % |
| | CH$_2$=CHSi(OC$_6$H$_{11}$)$_3$ | 48.3 weight % |

Using a filler, 0.1 g of the reaction product (composition) was dropped on No. 5C filter paper (the area of the circular section is 19.6 cm$^2$) to impregnate it by contact, and the filter paper was placed in an uncovered laboratory dish, to be left in a room, and the smell of cis-3-hexenol could be sensed by five persons even after seven days.

For comparison, 0.1 g of cis-3-hexenol was dropped onto the above-mentioned filter paper using a filler for impregnation by contact, the filter paper was placed in an uncovered laboratory dish and left in a room, and the smell of cis-3-hexenol could not be sensed by five persons after five hours.

A glass plate (100 mm long ×100 mm wide ×2 mm thick) to which 0.037 g of cis-3-hexenol was applied with a brush, and a glass plate to which 0.057 g of the reaction product (composition) used in Example 9 was applied with a brush, were left in a room, and the smell of cis-3-hexenol on both plates could not be sensed by five persons after three hours.

EXAMPLE 10

In a manner similar to that of Example 9, 40.9 g (equivalent to 0.3 mol) of methyltrimethoxysilane (CH$_3$Si(OCH$_3$)$_3$) (made by Tama Chemical Industry, Ltd.) and 92.6 g (equivalent to 0.6 mol) of geraniol (C$_{10}$H$_{17}$OH) (made by Tokyo Kasei Kogyo Co., Ltd.) were heated up to 155° C. to 190° C. in an atmosphere of nitrogen under normal pressure. Heating was stopped after 11 hours when the distillation of methanol ended. After methanol present in the reaction product was distilled and removed, the reaction product was analyzed by gas chromatography and the following results were obtained.

| | | |
|---|---|---|
| | C$_{10}$H$_{17}$OH | 4.2 weight % |
| | CH$_3$Si(OCH$_3$)$_2$(OC$_{10}$H$_{17}$) | 4.7 weight % |
| | CH$_3$Si(OCH$_3$)(OC$_{10}$H$_{17}$)$_2$ | 38.1 weight % |
| | CH$_3$Si(OC$_{10}$H$_{17}$)$_3$ | 51.2 weight % |

Using a filler, 0.4 g of the reaction product (composition) was dropped onto 5 g of boiling tips (spherical object about 2 mm in diameter, made by Katayama Chemical Industry, Ltd.) to be impregnated by contact, and placed in an uncovered laboratory dish, which was left in a room, and the smell of geraniol could be sensed by five persons after 30 days. For comparison, 0.4 g of geraniol (made by Tokyo Kasei Kogyo Co., Ltd.) was dropped onto 5 g boiling tips to be impregnated by contact, the boiling tips being placed in a laboratory dish to be left in a room, and the smell could not be sensed by five persons after 10 days.

EXAMPLE 11

In a manner similar to that of Example 9, 90.4 g (equivalent to 0.5 mol) of methyltriethoxysilane (CH$_3$Si(OC$_2$H$_5$)$_3$) (made by Tama Chemical Industry, Ltd.) and 151.7 g (equivalent to 1.5 mol) of trans-2-hexenol (C$_6$H$_{11}$OH) (Made by Chisso, Corp.) were heated up to 150° C. to 200° C. in an atmosphere of nitrogen under normal pressure. Heating was stopped after 12 hours when the distillation of ethanol ended. After ethanol present in the reaction product was distilled and removed under reduced pressure, the reaction product was analyzed by gas chromatography and the following results were obtained.

| | | |
|---|---|---|
| | C$_6$H$_{11}$OH | 11.7 weight % |
| | CH$_3$Si(OC$_2$H$_5$)$_2$(OC$_6$H$_{11}$) | 2.0 weight % |
| | CH$_3$Si(OC$_2$H$_5$)(OC$_6$H$_{11}$)$_2$ | 19.1 weight % |
| | CH$_3$Si(OC$_6$H$_{11}$)$_3$ | 65.5 weight % |

Using a filler, 0.8 g of the reaction product (composition) was dropped on a glass fiber filter (GA100, 0.25 mm thick, 25 cm$^2$ area, made by Toyo Filter Paper Co., Ltd.) to be impregnated by contact, which was placed in an uncovered laboratory dish to be left in a room, and the smell of trans-2-hexenol could be sensed by five persons after 20 days. For comparison, 0.8 g of trans-2-hexenol was dropped on the same glass fiber filter, using a filler, to be impregnated by contact, the filter being placed in an uncovered laboratory dish to be left in a room, and the smell could not be sensed by five persons after five days.

EXAMPLE 12

In a manner similar to that of Example 9, 90.3 g (equivalent to 0.5 mol) of methyltriethoxysilane (CH₃Si(OC₂H₅)₃) (made by Tama Chemical Ind.) and 184.6 g (equivalent to 1.5 mol) of β-phenylethyl alcohol (C₈H₉OH) (made by Kanto Kagaku, Ltd.) were heated up to 106° C. in the beginning and 195° C. in the end in an atmosphere of nitrogen under normal pressure. Heating was stopped after 8.5 hours when the distillation of ethanol ended. After ethanol present in the reaction product was distilled and removed, the reaction product was analyzed by gas chromatography, and the following results were obtained.

|  |  |
|---|---|
| C₈H₉OH | 27.3 weight % |
| CH₃Si(OC₂H₅)₂(OC₈H₉) | 7.7 weight % |
| CH₃Si(OC₂H₅)(OC₈H₉)₂ | 30.7 weight % |
| CH₃Si(OC₈H₉)₃ | 32.5 weight % |

Using a filler, 0.1 g of the reaction product (composition) was dropped on a polypropylene fiber non-woven fabric (ES-300S, about 4 mm thick, area 12 cm², made by Chisso Corp.) to be impregnated by contact, which was placed in an uncovered laboratory dish to be left in a room, and the smell of β-phenylethylalcohol could be sensed by five persons after 30 days. For comparison, 0.1 g of β-phenylethylalcohol was dropped on the same polypropylene fiber non-woven fabric using a filler, to be impregnated by contact, which was placed in an uncovered laboratory dish to be left in a room, and the smell could not be sensed by five persons after seven days.

What we claim is:

1. A silane compound of the formula:

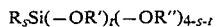

wherein R represents CH₃—, CH₃CH₂— or CH₂=CH—; R'O represents

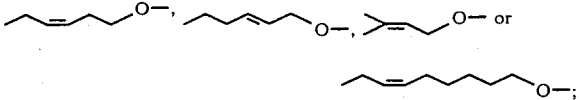

R"O represents CH₃O— or CH₃CH₂O—; s represents 0 or 1; and t represents an integer of from 1 to 4.

2. The silane compound of claim 1 wherein R'O is

3. The silane compound of claim 1 wherein R'O is

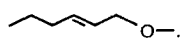

4. The silane compound of claim 1 wherein R'O is

5. The silane compound of claim 1 wherein R'O is

6. The silane compound of any one of claims 1 to 5 wherein s is 0.

7. The silane compound of any one of claims 1 to 5 wherein s is 1.

* * * * *